United States Patent [19]

Scherm et al.

[11] Patent Number: 4,602,037

[45] Date of Patent: Jul. 22, 1986

[54] XANTHATES AND ANTIVIRAL USE THEREOF

[75] Inventors: Arthur Scherm, Bad Homburg; Klaus Hummel, Frankfurt, both of Fed. Rep. of Germany

[73] Assignee: Merz+Co. GmbH & Co., Frankfurt, Fed. Rep. of Germany

[21] Appl. No.: 494,393

[22] Filed: May 13, 1983

Related U.S. Application Data

[63] Continuation-in-part of Ser. No. 324,581, Nov. 24, 1981.

[51] Int. Cl.[4] .................. A61K 31/265; C07C 154/02
[52] U.S. Cl. .................................... 514/512; 558/246
[58] Field of Search .................. 260/455 B; 424/301; 514/512

[56] References Cited

U.S. PATENT DOCUMENTS

| | | | |
|---|---|---|---|
| 2,811,432 | 10/1957 | Bruner | 260/455 B |
| 3,864,417 | 2/1975 | Hughes | 260/455 B |
| 3,864,469 | 2/1975 | Reiser et al. | 260/455 B |
| 3,965,137 | 6/1976 | Fancher | 260/455 B |

FOREIGN PATENT DOCUMENTS

| | | | |
|---|---|---|---|
| 5758/32 | 1/1932 | Australia | 260/455 B |
| 218423 | 6/1957 | Australia | 260/455 B |
| 17131 | 7/1970 | Australia | 260/455 B |
| 461052 | 3/1973 | Australia | 260/455 B |

OTHER PUBLICATIONS

Rodd, "Chemistry of Carbon Compounds", vol. IIA, pp. 140 and 423 (1953).

Chem. Abstract-193775b, Coskun, et al., vol. 83, 1975, p. 2.
Chem. Abstract-90991c, Rao, et al., vol. 80, 1974, p. 564.
Chem. Abstract-103552n, Gunduz, et al., vol. 80, 1974, p. 545.
Chem. Abstract-85: 103282c, Aihara, et al., vol. 85, 1976, p. 648.
Chem. Abstract-85: 184825g, Hasegawa, et al., vol. 85, 1976, p. 505.
Chem. Abstract-85767a, Paul, et al., vol. 81, 1974, p. 561.
Chem. Abstract-105933c, Paria et al., vol. 82, 1975, p. 575.
Chem. Abstract-139231n, Silhanek et al., vol. 82, 1975, p. 555.
Chem. Abstract-111226r, Harano, et al., vol. 82, 1975, p. 441.
Chem. Abstract-155401y, Gleim, et al., vol. 82, 1975, p. 527.
Chem. Abstract-47881t, Silhanek, et al., vol. 77, 1972, p. 435.
Chem. Abstract-33453s, Hayashi et al., vol. 83, 1975, p. 346.

*Primary Examiner*—Henry R. Jiles
*Assistant Examiner*—Robert C. Whittenbaugh
*Attorney, Agent, or Firm*—Gordon W. Hueschen

[57] ABSTRACT

Novel antiviral xanthate compounds, a process for their production, pharmaceutical compositions containing said xanthate compounds, and a method of combating viruses therewith, are disclosed.

60 Claims, No Drawings

XANTHATES AND ANTIVIRAL USE THEREOF

The present application is a continuation-in-part of our prior-filed copending U.S. application Ser. No. 324,581, filed Nov. 24, 1981.

The invention relates to new xanthate compounds, a process for the manufacture thereof, compositions containing these compounds, and method of treating viruses therewith.

A few alkyl xanthates are already known. They have hitherto been used as flotation auxiliaries, pesticides, herbicides and vulcanization accelerators (cf. Ullmann's Enzylopädie der technischen Chemie, 3rd Edition, Volume XVIII, pp. 718–728).

The aim of the present invention is to provide xanthates with acceptable pharmacological properties.

Unexpectedly, it was found that certain xanthates exhibit beneficial antimicrobial and antiviral effects.

Subject matter of the invention are therefore xanthates having the general formula I:

wherein
$R^1$ is adamantyl, norbornyl, tricyclodecyl, benzyl, straight or branched $C_3$-$C_{20}$-alkyl, $C_3$-$C_{20}$-cycloalkyl, furyl, pyridyl or quinuclidinyl, and wherein the aforementioned straight or branched $C_3$-$C_{20}$-alkyl group may be substituted by a hydroxy, $C_1$-$C_4$-alkoxy group or a halogen atom, and wherein the aforementioned $C_3$-$C_{20}$-cycloalkyl group may likewise be substituted by a hydroxy, $C_1$-$C_4$-alkoxy or $C_1$-$C_4$-alkyl group or a halogen atom, and wherein
$R^2$ is a mono- or polyvalent metal atom, a straight or branched $C_1$-$C_6$-alkyl group which may be substituted by a hydroxy, $C_1$-$C_4$-alkoxy, amino, $C_1$-$C_4$-alkylamino, $(C_1$-$C_4$-alkyl$)_2$ amino or $(C_1$-$C_4$-alkyl$)_3$ ammonium group or a halogen atom, or represents a 2,3-dihydroxypropyl or ω-hydroxy($C_1$-$C_4$-alkoxy) methyl group.

If $R^1$ is a straight or branched $C_3$- to $C_{20}$ alkyl group, it may represent, for example, propyl, butyl, pentyl, hexyl, heptyl, octyl, nonyl, decyl, undecyl, dodecyl, tridecyl, tetradecyl or pentadecyl groups, in straight, mono- or multiple-branch form, preferably n-hexyl, n-decyl, n-dodecyl and n-tetradecyl groups. The cycloalkyl groups preferably used are the cyclopentyl, cyclohexyl, cycloheptyl, cyclooctyl, cyclononyl, cyclodecyl, cycloundecyl, cyclododecyl, cyclotridecyl, cyclotetradecyl and cyclopentadecyl groups. Utmost preference is given to the cyclohexyl and cyclododecyl groups. Bi- and tricyclic groups are also included.

The aforementioned halogen atoms comprise fluorine, chlorine, bromine and iodine. Chlorine or bromine are preferably used in halogen substitution.

If $R^2$ is a metal atom, it is preferably a monovalent metal, i.e., sodium or potassium.

The compounds according to the invention may be produced according to generally known methods by reacting an alcoholate of the formula $R^1$—O—Me, wherein $R^1$ represents the aforementioned definitions and Me is an alkali metal atom, with carbon disulfide, or by reacting an alcohol of the formula $R^1$—OH, wherein $R^1$ represents the aforementioned definitions, with carbon disulfide in the presence of a strong alkali. This results in compounds of formula I, wherein $R^2$ is an alkali metal atom. For preparing the compounds of formula I, wherein $R^2$ represents one of the other aforementioned definitions, an alkali xanthate of formula I is reacted in an inert solvent with an alkylating agent appropriate to the $R^2$ group.

The drugs according to the invention contain at least one of the aforementioned compounds having the general formula I, in a commonly used solid or liquid carrier. With drugs $R^1$ may also be a methyl or ethyl group. The compounds according to the invention may also be combined with known actives. The compounds according to the invention are characterized by an antimicrobial, especially antiviral action. The antiviral range of action comprises, for example, herpes and influenza viruses.

In-vitro investigations by means of plaque reduction tests on various virus strains showed an inhibition of growth at substance concentrations ranging from 1 to 100 μg/ml. The toxicity of the substances according to the invention is relatively low. The substances may, above all, be used as effective preventives of influenza and herpetic affections of the skin and mucous substances. The daily dose to be administered to adults in the course of the disease is about 5–100 mg of the active per day.

If the compounds according to the invention are administered by the parenteral, subcutaneous, intravenous, intramuscular and intraperitoneal route, the carrier is a sterile liquid such as water or oil, the oils being of vegetable, animal or synthetic origin. Glucose solutions are usually used for injectable solutions. In general, the liquid carriers of the injectable solutions contain 0.5–25 percent by weight of the active substance. The compounds according to the invention may also be successfully administered by the oral route, and are likewise suited for the treatment of pneumonias by applying them in vapor or spray form in the oronasal region. Best suited for oral administration are tablets, capsules, powders, solutions, suspensions or elixirs. With these administration forms the contents of the active ingredient is at least 2 percent by weight, related to the total weight of the composition.

The invention will be further illustrated by the following examples: (Melting points are in degrees Centigrade).

EXAMPLE 1: Sodium cyclododecyl xanthate 100 g (0.54 mol) of cyclododecanol is heated to 100° C., 2.5 g (0.11 mol) of sodium is added, the temperature of the mixture being maintained at 220° C. for 1 hour. The product is poured into a porcelain dish, pulverized after cooling, the powder being suspended in ether (400 ml), 9 g (0.12 mol) of carbon disulfide being added drop by drop. After the addition of 200 ml of water, the aqueous phase is separated, and 20 g of NaCl added. The precipitate is filtered and recrystallized twice from alcohol (120 ml).

Yield: 17 g (56% of the theoretical value).
Mp: 218°–219°$_{decomposition}$.

| | Elementary analysis | |
| --- | --- | --- |
| | calculated | found |
| C | 55.32 | 54.42 |
| H | 8.16 | 8.08 |
| S | 22.69 | 21.90 |

In the same manner, the corresponding potassium salt is produced by employing potassium instead of sodium.

EXAMPLE 2: Sodium benzyl xanthate 4.6 g (0.2 mol) of sodium is added to 108 g (1 mol) of benzyl alcohol under nitrogen. The mixture is heated to 160° C. for 2 hours, poured into a porcelain dish, and allowed to cool. The semi-solid product is suspended in ether (400 ml), 15.2 g (0.2 mol) of carbon disulfide is added dropwise, and the mixture heated under reflux for 1 hour. The reaction solution is allowed to cool, the precipitate being filtered and washed with ether.

Yield: 16 g (39% of the theoretical value).
Mp: >180°$_{decomposition.}$

|   | Elementary analysis | | |
|---|---|---|---|
|   | calculated | found | |
| C | 42.86 | 43.05 | ($C_8H_7Na\ OS_2 \times H_2O$) |
| H | 4.02 | 4.31 | |
| S | 28.57 | 26.78 | |

In the same manner, the corresponding potassium salt is produced by employing potassium instead of sodium.

EXAMPLE 3: Sodium cyclohexyl xanthate 3.6 g (0.16 mol) of sodium is added to 100 ml (1 mol) of cyclohexanol under nitrogen, and heated under reflux until complete reaction of the sodium has taken place. The reaction solution is poured into a porcelain dish and pulverized after cooling. The powder is suspended in ether (400 ml) and heated to reflux for 15 min. After cooling, 12.8 g (0.17 mol) of carbon disulfide is added dropwise. After the addition of 200 ml of water, the aqueous phase is separated, and 40 g of NaCl added. The precipitate is filtered, washed with ether and dried.

Yield: 25 g (75% of the theoretical value).
Mp: 22 200°$_{decomposition.}$

|   | Elementary analysis | |
|---|---|---|
|   | calculated | found |
| C | 42.42 | 42.21 |
| H | 5.55 | 5.52 |
| S | 32.32 | 31.87 |

In the same manner, the corresponding potassium salt is produced by employing potassium instead of sodium.

In the same manner, starting from n-hexanol, the corresponding sodium and potassium n-hexyl xanthates are prepared and found to be active virustatic agents.

EXAMPLE 4: Cyclohexyl methyl xanthate 3 g (0.015 mol) of sodium cyclohexyl xanthate is dissolved in 50 ml of dried methanol and heated to reflux with 10.7 g (0.075 mol) of methyl iodide for 1 hour. After cooling, the reaction solution is evaporated by using a rotary evaporator, dissolved in ether/water (50/50), the ether phase being separated and dried with sodium sulfate, purified with active carbon/bleaching earth, and evaporated with the aid of a rotary evaporator.

Yield: 2 g (70% of the theoretical value).

|   | Elementary analysis | |
|---|---|---|
|   | calculated | found |
| C | 50.52 | 50.47 |
| H | 7.36 | 7.28 |

EXAMPLE 5: Potassium adamantyl xanthate 15.2 g (0.1 mol) of adamantanol is dissolved in dried tetrahydrofurane, nitrogen is introduced into the solution and 2 g of potassium (0.05 mol) is added. The solution is heated under reflux for 10 hours. After cooling, the product is suspended in 200 ml of ether and heated to reflux for 15 minutes. 3.8 g (0.05 mol) of carbon disulfide is added, and the solution is heated again for 45 minutes under reflux. After cooling, 200 ml of water is added. The aqueous phase is separated, 25 g of NaCl added, and the precipitate filtered.

Yield: 2 g (8% of the theoretical value).
Mp: >300°$_{decomposition.}$

|   | Elementary analysis | |
|---|---|---|
|   | calculated | found |
| C | 49.60 | 49.82 |
| H | 5.63 | 5.66 |
| S | 24.05 | 23.50 |

In the same manner, the corresponding sodium salt is produced by employing sodium instead of potassium.

EXAMPLE 6: Potassium 2-endo-bicyclo[2.2.1$^{1,4}$]-heptyl xanthate 340 g (about 3 mole) of endo-norborneol is melted (160° C.) under nitrogen atmosphere and reacted in portions with a total of 19.55 g (0.5 mol) of crust-free potassium. The temperature is maintained at 160° until complete dissolution of the metal has taken place. Subsequently, excess norborneol is distilled off, the colorless residue dried under high vacuum for a short time, and dissolved in 500 ml of absolute tetrahydrofurane. With cooling, 31 ml (0.5 mol) of carbon disulfide—dissolved in 150 ml of absolute ether—is added to this alcoholate drop by drop. The reaction mixture is stirred for 1 hour at 40° C. The xanthate separating already in the course of the reaction as a pale yellow precipitate is precipitated to a large extent by the addition of 1 l of dry ether. The precipitate is suction filtered and thoroughly rinsed with ether on the suction filter apparatus. The xanthate crystallizes from concentrated alcoholic solution by forming fine, pale yellow needles.

Yield: 95 g (83% of the theoretical value).
Mp: 256°–258°$_{decomposition.}$

|   | Elementary analysis | |
|---|---|---|
|   | calculated | found |
| C | 42.44 | 42.40 |
| H | 4.90 | 4.92 |
| S | 28.32 | 27.90 |

In the same manner, the corresponding sodium salt is produced by employing sodium instead of potassium.

EXAMPLE 7: Potassium 8(9)-tricyclo[5.2.1.0$^{2,6}$]decyl xanthate 457 g (about 3 mol) of tricyclo[5.2.1.0$^{2,6}$]decanol-8(9) (TCD alcohol A, isomer mixture distributed by Hoechst AG) is reacted under protective gas atmosphere (nitrogen) in portions with a total of 19.55 g (0.5 mol) of crust-free potassium with stirring at 150°-160° C. The temperature of the mixture is kept at this level until complete reaction of the metal has taken place. Subsequently, excess alcohol is distilled off under vacuum, the alcoholate being dried under high vacuum and dissolved in 500 ml of absolute tetrahydrofurane. With cooling, 31 ml (0.5 mol) of carbon disulfide in 150 ml of absolute ether is gradually added to the reaction solution. The mixture is stirred for 1 hour at 40° C., the xanthate is precipitated by adding 1 l of dry ether, suction filtered and thoroughly rinsed with ether on the suction filter apparatus. After recrystallization from ethanol, fine pale yellow crystals are obtained.

Yield: 104 g (78% of the theoretical value).

Mp: $260°_{decomposition}$.

|   | Elementary analysis | |
|---|---|---|
|   | calculated | found |
| C | 49.58 | 49.60 |
| H | 5.67 | 5.62 |
| S | 24.07 | 24.19 |

In the same manner, the corresponding sodium salt is produced by employing sodium instead of potassium.

The compounds according to the invention are characterized by valuable pharmacodynamic properties and may, therefore, be successfully applied in human and veterinary medicine.

The virustatic properties have been demonstrated by the in-vitro testing of virus inhibition in an inhibition areola (plaque inhibition test) and by the plaque reduction method. The following virus strains were used:

Influenza A2
Vaccine virus
Herpes virus

In this plaque inhibition test tissue cultures of influenza and vaccine viruses (chick fibroblasts), parainfluenza (monkey renal epithelial cells) and herpes viruses (human amnion cells) are infected in such a manner that closely packed but individual plaques form. The test substance is then applied as a 1% solution, and the diameter of the inhibition areola is determined. The results are represented in the following table.

TABLE 1

Virustatic properties of the compounds according to the invention demonstrated in the plaque inhibition test Substance concentration: $R^1-O-C\begin{smallmatrix}S\\\\SR^2\end{smallmatrix}$ .200γ/0.02 ml

| R¹ | R² | Virustatic properties | | |
|---|---|---|---|---|
|   |   | Influenza | Vaccine | Herpes |
| Cyclododecyl | Na | +++ | +++ | +++ |
| n-Dodecyl | Na | +++ | +++ | +++ |
| Cyclohexyl | Na | ++ | +++ | +++ |
| Benzyl | Na | + | + | + |
| 1-Norbornyl | Na | ++ | +++ | +++ |
| 1-Adamantyl | K | + | + | + |
| Standard 1-Aminoadamantane hydrochloride |   | +++ | 0 | 0 |

IA = inhibition areola
0 = no inhibition areola
+ = moderate (IA 10–20 mm)
++ = good (IA 20–30 mm)
+++ = very good (IA > 30 mm)

The action of the test substances on various virus strains has also been determined by in-vitro plaque reduction tests. After the application of the test substance, followed by infection with the respective viruses and incubation, the number of plaques produced by the viruses is determined. The smaller the number of plaques is in comparison with the control, the more effective is the substance under testing. The test results are summarized in the following table;

TABLE 2

Virustatic action of the compounds according to the invention demonstrated in the plaque reduction test

| Substance | Concentration | Plaque reduction in % |
|---|---|---|
| Sodium cyclododecyl xanthate | 20γ/ml | 100 |
| Sodium dodecyl xanthate | 20γ/ml | 100 |
| Sodium cyclohexyl xanthate | 20γ/ml | 100 |
| Standard aminoadamantane hydrochloride | 20γ/ml | 10 |

Tables 1 and 2 show the superior virustatic action of the compounds according to the invention.

Method of Treating, i.e., Controlling Viruses

The antiviral treatment of a host suffering from such insufficiency, comprising the step of administering to the patient, host, or situs suffering from such viral contamination or infection the selected xanthate of the foregoing formula I in an antiviral amount effective for such purpose by the oral, topical, or parenteral route, the said amount administered preferably being 10 to 100 mg per dosage unit by the oral route or 0.05 to 5 mg per dosage unit by parenteral route, constitutes the method-of-treating embodiment of the present invention, in its broadest concepts. Representative dosage forms follow.

The dosages of xanthates in general will approximate the dosages of the standard aminoadamantane hydrochloride antiviral agent and, in many cases, because of the enhanced antiviral activity of the xanthate compounds, will be considerably less.

Dosage Forms

Unit dosage forms for antiviral or other use according to the present invention may be of any suitable and/or conventional type. For oral administration, the unit dosage form generally contains about 10 to 100 mg of selected active ingredient, whether xanthate ester or salt, preferably about 50 mg thereof. For parenteral administration in sterile solution, the unit dose usually contains 0.05 to 5 mg of the active ingredient selected, preferably about 2.5 mg thereof. As already stated, the selected compound is preferably administered together or in conjunction with a pharmaceutically-acceptable carrier, and preferably in the form of a tablet.

According to the usual practice of the art, the active xanthate compound is therefore generally associated with a non-toxic pharmaceutical diluent or carrier which may be either a solid material or a liquid. Bland carriers are preferred for some applications. The composition can take the form of tablets, powders, capsules, liquid solutions, emulsions or suspensions, or other dosage forms which are particularly useful for oral administration. Liquid or semi-liquid diluents may be employed for oral use. Such a medium can be or contain a solvent such as water. The only basic limitations of the liquid diluent used are compatibility and palatability. The compositions can take the form of the selected xanthate admixed with solid diluents and/or tableting adjuvants such as rice starch, corn starch, potato starch, lactose, sacharose, gelatin, talc, stearic acid, magnesium stearate, carboxymethylcellulose, gums such as gum acacia or tragacanth, chicle, agar agar, or the like. When in liquid form, the composition may be a sterile or non-sterile solution, suspension, dispersion, elixir, or the like, all as is well known in the art. For topical application, the composition may, e.g., be in solution, lotion, ointment, salve, tincture, or like form.

It is to be understood that the invention is not to be limited to the exact details of operation or exact compounds, compositions, methods, or procedures shown and described, as obvious modifications and equivalents will be apparent to one skilled in the art.

EXAMPLE 8: Potassium 2-exo-bicyclo[2.2.1$^{1,4}$]-heptyl xanthate (D611-exo-K)

In exactly the same manner as given in Example 6, this compound is prepared starting from potassium, exonorborneol and carbon disulfide. The analysis is the same as in Example 6. The melting point is 249–252 degrees Centigrade (with decomposition). The antiviral activities are essentially identical with those of the compound D611, including $IC_{50}$ values.

The sodium and any other alkali metal salt thereof is prepared in essentially the same manner starting from the selected alkali metal or alkali metal norborneolate and found to have essentially the same antiviral activity as D611.

EXAMPLE 9: Sodium 2-endo-bicyclo[2.2.1$^{1,4}$]-heptyl xanthate (D611Na)

The sodium salt of the compound of Example 6 is sodium 2-endo-bicyclo[2.2.1$^{1,4}$]-heptyl xanthate, prepared as set forth in that Example, but starting from endonorborneol and sodium, has the melting point 246–248 degrees Centigrade (with decomposition), and is found to have essentially the identical antiviral activity as the corresponding potassium salt (D611).

Other alkali metal salts are prepared in essentially the same manner starting from the selected alkali metal or alkali metal norborneolate and are found to have essentially the same antiviral activity as D611.

EXAMPLE 10: Potassium 4(or para)-isobornylcyclohexyl xanthate (D622)

Thirty-nine grams (1 mol) of potassium are added in small portions under nitrogen atmosphere to 945 grams (4 mol) of essentially pure 4(or para)-isobornylcyclohexanol at 100–150 degrees Centigrade. After complete reaction of the potassium, the solution is cooled to forty degrees Centigrade and diluted with one liter of anhydrous tetrahydrofuran. Then 66.6 ml (1.1 mol) of carbon disulfide is added slowly and the reaction mixture maintained at forty degrees Centigrade thereafter for four hours. After addition of two liters of petroleum ether, the xanthate is filtered and thereafter recrystallized from two liters of ethanol.

Yield: 68 g (20% of the theoretical value).

Mp: 262 degrees Centigrade (with decomposition).

| Elementary Analysis | | |
|---|---|---|
| | calculated | found |
| C | 58.24 | 58.26 |
| H | 7.76 | 7.70 |
| S | 18.29 | 18.14 |

The $IC_{50}$ value in micrograms per milliliter in the plaque-reduction assay for this compound against Herpes simplex virus is 1.9. (HSV-I, especially strain HSV-I-ISO 3.) Otherwise, its antiviral activity is essentially identical with that for the compound D609, but somewhat superior thereto.

The potassium 2 (or ortho) compound corresponding to D622 and the corresponding sodium and any other alkali metal salt thereof or corresponding to D622 is prepared in essentially the same manner starting from the selected potassium 2 (or ortho)-isobornylcyclohexanoate or another selected alkali metal or alkali metal isobornylcyclohexanoate and found to have essentially the same antiviral activity as D622.

ADDITIONAL ANTIVIRAL PROPERTIES OF THE COMPOUNDS OF THE INVENTION

The compounds of the invention are active in the plaque-reduction test, a standard test for determining antiviral activity and potency, as already stated. One such standard direct plaque assay is that described by E. C. Herrmann Jr. et al., Proc. Soc. Exptl. Biol. Med. 103, 625 (1980). This is the test procedure first employed and its principle is well established. It involves the following: Tissue culture cells are grown in small wells as monolayers and infected with appropriate virus dilutions. They are then overlayed with semisolid media to prevent spreading of the viral progeny to originally-uninfected cells. From the infected cells alone, foci of secondary infections develop within three (3) days, and these can be visualized as plaques after appropriate staining according to well-known procedure. To determine the inhibitory effect of a compound, the compound is administered directly onto the infected cells prior to the addition of the overlay, and the virus yield is then compared with the yield from untreated infected cell cultures. The percentage of plaque reduction or inhibition is then expressed in comparison with the 100% plaque-forming units (PFU) as taken from the uninhibited control.

A refined plaque reduction assay was subsequently adopted, to eliminate the possibility of error due to the fact that plaques arising in infected, threated cultures are not simply reduced in their total number, but rather tend to shrink. Sometimes they shrink to the extent that they may escape detection despite their presence in undiminished numbers, giving rise to a false determination of the number of plaques present and, accordingly, the extent of plaque reduction. The refined method, which is not subject to this disadvantage, involves assaying the virus-containing fluid from the treated cultures without a semisolid overlay in a subsequent plaque assay, according to the procedure described, for example, by Schinazi, R. F. and Nahmias, A. J., in the American Journal of Medicine 73, 40–48 (1982), in which case plaques of normal size develop so that reproducible quantitative titrations are made feasible.

The compounds of the invention were found to be effective antiviral agents when thus evaluated against numerous different representative virus types. In addition to Influenza A2, Vacciniavirus, Coxsackie B5, and VSV, the virus types included specifically the following types of Herpes virus: Herpes simplex virus (HSV) Type I, which includes strains A NG, ISO 3, ISO 6, and WA, and Herpes simplex virus (HSV) Type II, which includes strain HG 52 (the genital herpes).

When compared with the uninhibited control, plaque reduction with a compound of the invention at twenty micrograms per milliliter was on the order of the following:

| Viral strain | Percentage PFU compared with control at 100% |
|---|---|
| Coxsackie B5 | 4 |
| HSV-I | 2.5 |
| HSV-I-ISO 3 | 1.05 |
| HSV-I-WA | 0.9 |
| HSV II-HG-52 | 0.3 |
| HSV I-ISO 6 | 0.1 |
| VSV | 0.05 |
| HSV-I-A NG | 0.1 (5.5 micrograms/ml.) |

Accordingly, the viral activity of the compounds of the invention as evidenced by the plaque-reduction assay is indeed substantial. The percentage PFU figures given are for the compound D609, but similar figures are obtained in the test for other compounds of the invention, including especially D611, D435, mixtures of the compounds, e.g., D435 and D611 or D435 and D609, and so on.

When tested by the refined procedure outlined above at the same pH and other environmental conditions, and against the same viral strain, the compounds of the invention gave the following quantitative results, expressed in terms of $IC_{50}$ (micrograms per milliliter), the amount of the compound thus being expressed as the minimum inhibitory concentration required to produce a 50% reduction in plaque forming units (PFU) as compared with the untreated control.

| $R^1$ | $R^2$ | $IC_{50}$ |
|---|---|---|
| benzyl (Ex 2) | Na | >30 |
| cyclohexyl (Ex 3) | Na | 9.5 |
| n-dodecyl | Na | 7.0 |
| 1-adamantyl (D424) (Ex 5) | K | >10 |
| tricyclodecyl (D609) (Ex 7) | K | 3.0 |
| 1-norbornyl (D611) (Ex 6) | K or Na | 3.0 |
| cyclododecyl (D435) (Ex 1) | Na | 2.5 |

The compounds of the present invention are accordingly established by the plaque reduction or inhibition assay as being potent antiviral agents.

Further tests were conducted to determine the development of resistance by viral strains against compounds of the invention. Accordingly, compounds of the invention were tested from this standpoint against selected herpes viruses according to the following protocol: Infected cells were maintained over prolonged periods of time under suboptimal concentrations of the test compound and the viral progeny was passaged manifold under the same conditions. Thereafter, the resulting virus pool was compared with wild-type virus regarding its ability to respond to the inhibitory action of the test compound. As a result of this test procedure, it was determined that, in no cases and under no conditions did resistance develop against the test compound in the virus strain evaluated. Representatively, the resistance determinations were made with respect to the compounds D435, D609, D611, a combination of the compounds, e.g., D435 and D611 or D435 and D609, as well as other compounds of the invention, with the stated result that, under no conditions was resistance found to have developed.

The sensitivity of the assay for possible resistance was sufficient to detect any mutation which would have been induced under the experimental conditions employed in the study. The importance of this result, the finding of no generation of resistance, is obvious, since antiviral compounds with initially effective antiviral action may well develop resistance in the viral strain treated, and thus become a potential hazard. It is to be noted that recently-published information concerning the antiviral drug Acyclovir (Burns et al., The Lancet, Feb. 20, 1982) is to the effect that treatment of two immunosuppressed patients with Acyclovir gave rise to the production of herpes virus mutants, which were considerably less susceptible to treatment with that particular drug than the initially-recognized virus. The absence of the development or generation of resistance is obviously a great advantage when considering the compounds of the present invention as antiviral agents.

The test compounds, especially D609, appeared to exert their antiviral activity most effectively at a pH of 6.8 as compared with slightly higher pHs of 7.25–7.8.

We claim:

1. Xanthates of the formula:

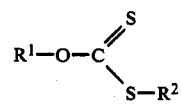

wherein $R^1$ is norbornyl, tricyclodecyl, or cyclododecyl, and wherein $R^2$ is a mono- or polyvalent metal atom, a straight or branched $C_1$–$C_6$-alkyl group which may be substituted by a hydroxy, $C_1$–$C_4$-alkoxy, amino, $C_1$–$C_4$-alkylamino or $(C_1$–$C_4$-alkyl$)_2$ amino group or $(C_1$–$C_4$-alkyl$)_3$ ammonium group or a halogen atom, or represents a 2,3-dihydroxypropyl group or ω-hydroxy-$(C_1$–$C_4$-alkoxy)methyl group.

2. Compound of claim 1, which is alkali metal cyclododecyl xanthate.

3. Composition of claim 1, wherein the antiviral compound is alkali metal benzyl xanthate.

4. Composition of claim 1, wherein the antiviral compound is alkali metal cyclohexyl or dodecyl xanthate.

5. Compound of claim 1, which is alkali metal adamantyl xanthate.

6. Compound of claim 1, which is alkali metal-2-endobicyclo[2.2.1$^{1,4}$]heptyl xanthate.

7. Compound of claim 1, which is alkali metal 8(9)-tricyclo[5.2.1.0$^{2.6}$]decyl xanthate.

8. Product of claim 1, which is sodium cyclododecyl xanthate.

9. Composition of claim 1, wherein the antiviral compound is sodium benzyl xanthate.

10. Composition of claim 1, wherein the antiviral compound is sodium cyclohexyl or dodecyl xanthate.

11. Composition of claim 1, wherein the antiviral compound is cyclohexyl methyl xanthate.

12. Product of claim 1, which is potassium adamantyl xanthate.

13. Product of claim 1, which is potassium 2-endobicyclo[2.2.1$^{1,4}$]heptyl xanthate.

14. Product of claim 1, which is potassium 8(9)-tricyclo[5.2.1.0$^{2,6}$]decyl xanthate.

15. A pharmaceutical composition having virustatic properties against herpes, influenza, or vaccine virus which comprises an effective antiviral amount of a compound of claim 1 in admixture with a pharmaceutically-acceptable carrier.

16. A method of combating a herpes, influenza, or vaccine virus which is susceptible to inhibition by a chemical antiviral agent comprising the step of administering to the host or situs for the virus an effective antiviral amount of a compound according to claim 1.

17. A compound of claim 1, which is an alkali metal xanthate.

18. A composition of claim 1, wherein the antiviral compound is cyclohexyl lower-alkyl xanthate.

19. A composition having virustatic properties against herpes, influenza, or vaccine virus which comprises an effective antiviral amount of a compound of claim 1 in admixture with a carrier which does not interfere with the antiviral effect of the active antiviral compound.

20. A biologically-active composition having virustatic properties against herpes, influenza, or vaccine virus which comprises an effective antiviral amount of a xanthate of the formula:

$$R^1-O-C\underset{S-R^2}{\overset{S}{\diagup\!\!\!\!\diagdown}}$$

wherein $R^1$ is benzyl, straight or branched $C_3-C_{20}$-alkyl, or $C_3-C_{20}$-cycloalkyl, wherein the aforementioned straight or branched $C_3-C_{20}$-alkyl group may be substituted by a hydroxy, $C_1-C_4$-alkoxy group, or a halogen atom, and wherein the aforementioned $C_3-C_{20}$-cycloalkyl group may be likewise substituted by a hydroxy, $C_1-C_4$-alkoxy, or $C_1-C_4$-alkyl group, or a halogen atom, and wherein $R^2$ is a mono- or polyvalent metal atom, a straight or branched $C_1-C_6$-alkyl group which may be substituted by a hydroxy, $C_1-C_4$-alkoxy, amino, $C_1-C_4$-alkylamino, or $(C_1-C_4$-alkyl$)_2$ amino group, or $(C_1-C_4$-alkyl$)_3$ ammonium group, or a halogen atom, or represents a 2,3-dihydroxypropyl group or ω-hydroxy-$(C_1-C_4$-alkoxy)methyl group, in admixture with a carrier which does not interfere with the antiviral effect of the active antiviral compound.

21. A composition of claim 20, wherein the antiviral compound is an alkali metal xanthate.

22. A composition of claim 15, wherein the antiviral compound is alkali metal cyclododecyl xanthate.

23. A composition of claim 15, wherein the antiviral compound is alkali metal adamantyl xanthate.

24. A composition of claim 15, wherein the antiviral compound is alkali metal 2-endo-bicyclo[2.2.1$^{1,4}$]heptyl xanthate.

25. A composition of claim 15, wherein the antiviral compound is alkali metal 8(9)-tricyclo[5.2.1.0$^{2.6}$]decyl xanthate.

26. A composition of claim 15, wherein the antiviral compound is sodium cyclododecyl xanthate.

27. A composition of claim 15, wherein the antiviral compound is potassium adamantyl xanthate.

28. A composition of claim 15, wherein the antiviral compound is potassium 2-endo-bicyclo[2.2.1$^{1,4}$]heptyl xanthate.

29. A composition of claim 15, wherein the antiviral compound is potassium 8(9)-tricyclo[5.2.1.0$^{2.6}$]decyl xanthate.

30. A method of combating a herpes, influenza, or vaccine virus which is susceptible to inhibition by a chemical antiviral agent comprising the step of administering to the host or situs for the virus an effective antiviral amount of a xanthate of the formula:

$$R^1-O-C\underset{S-R^2}{\overset{S}{\diagup\!\!\!\!\diagdown}}$$

wherein $R^1$ is benzyl, straight or branched $C_3-C_{20}$-alkyl, or $C_3-C_{20}$-cycloalkyl, wherein the aforementioned straight or branched $C_3-C_{20}$-alkyl group may be substituted by a hydroxy, $C_1-C_4$-alkoxy group, or a halogen atom, and wherein the aforementioned $C_3-C_{20}$-cycloalkyl group may be likewise substituted by a hydroxy, $C_1-C_4$-alkoxy, or $C_1-C_4$-alkyl group, or a halogen atom, and wherein $R^2$ is a mono- or polyvalent metal atom, a straight or branched $C_1-C_6$-alkyl group which may be substituted by a hydroxy, $C_1-C_4$-alkoxy, amino, $C_1-C_4$-alkylamino, or $(C_1-C_4$-alkyl$)_2$ amino group, or $(C_1-C_4$-alkyl$)_3$ ammonium group, or a halogen atom, or represents a 2,3-dihydroxypropyl group or ω-hydroxy-$(C_1-C_4$-alkoxy)methyl group.

31. A method of claim 30, wherein the antiviral compound is an alkali metal xanthate.

32. A method of claim 16, wherein the antiviral compound is alkali metal cyclododecyl xanthate.

33. A method of claim 16, wherein the antiviral compound is alkali metal adamantyl mixture.

34. A method of claim 16, wherein the antiviral compound is alkali metal 2-endo-bicyclo[2.2.1$^{1,4}$]heptyl xanthate.

35. A method of claim 16, wherein the antiviral compound is alkali metal 8(9)-tricyclo[5.2.1.0$^{2.6}$]decyl xanthate.

36. A method of claim 16, wherein the antiviral compound is sodium cyclododecyl xanthate.

37. A method of claim 16, wherein the antiviral compound is potassium adamantyl xanthate.

38. A method of claim 16, wherein the antiviral compound is potassium 2-endo-bicyclo[2.2.1$^{1,4}$]heptyl xanthate.

39. A method of claim 16, wherein the antiviral compound is potassium 8(9)-tricyclo[5.2.1.0$^{2.6}$]decyl xanthate.

40. A method of claim 30, wherein the antiviral compound is alkali metal benzyl xanthate.

41. A method of claim 30, wherein the antiviral compound is alkali metal dodecyl or cyclohexyl xanthate.

42. A method of claim 30, wherein the antiviral compound is sodium benzyl xanthate.

43. A method of claim 30, wherein the antiviral compound is sodium cyclohexyl or dodecyl xanthate.

44. A method of claim 30, wherein the antiviral compound is cyclohexyl methyl xanthate.

45. A method of claim 30, wherein the antiviral compound is a cyclohexyl lower-alkyl xanthate.

46. Alkali metal isobornylcyclohexyl xanthate.

47. Compound of claim 46, which is Potassium 4-isobornylcyclohexyl xanthate.

48. A pharmaceutical composition suitable for use against herpes, vaccinia, or influenza virus comprising an effective antiviral amount of a compound of claim 46 together with a pharmaceutically-acceptable pharmaceutical carrier.

49. A pharmaceutical composition suitable for use against herpes, vaccinia, influenza virus comprising an effective antiviral amount of a compound of claim 47 together with a pharmaceutically-acceptable pharmaceutical carrier.

50. A method of combating a herpes, vaccinia or influenza virus comprising administering to the host an effective antiviral amount of a compound of claim 46.

51. A method of combating a herpes, vaccinia or influenza virus comprising administering to the host an effective antiviral amount of a compound of claim 47.

52. Alkali metal 2-bicyclo[2.2.1$^{1,4}$]-heptyl xanthate.

53. Compound of claim 52, which is Alkali metal 2-exo-bicyclo[2.2.1$^{1,4}$]-heptyl xanthate.

54. Compound of claim 52, which is Potassium 2-exo-bicyclo[2.2.1$^{1,4}$]-heptyl xanthate.

55. A pharmaceutical composition suitable for use against herpes, vaccinia, or influenza virus comprising an effective antiviral amount of a compound of claim 52 together with a pharmaceutically-acceptable pharmaceutical carrier.

56. A pharmaceutical composition suitable for use as an antiviral composition or antitumor composition against herpes, vaccinia, or influenza virus comprising an effective antiviral amount of a compound of claim 53 together with a pharmaceutically-acceptable pharmaceutical carrier.

57. A pharmaceutical composition suitable for use as an antiviral composition or antitumor composition against herpes, vaccinia, or influenza virus comprising an effective antiviral amount of a compound of claim 54 together with a pharmaceutically-acceptable pharmaceutical carrier.

58. A method of combating a herpes, vaccinia, or influenza virus comprising administering to the host an effective antiviral amount of a compound of claim 52.

59. A method of combating a herpes, vaccinia, or infuenza virus comprising administering to the host an effective antiviral amount of a compound of claim 53.

60. A method of combating a herpes, vaccinia, or influenza virus comprising administering to the host an effective antiviral amount of a compound of claim 54.

* * * * *

UNITED STATES PATENT AND TRADEMARK OFFICE
CERTIFICATE OF CORRECTION

PATENT NO. : 4,602,037       PAGE 1 of 2

DATED : July 22, 1986

INVENTOR(S) : Arthur Scherm and Klaus Hummel

It is certified that error appears in the above-identified patent and that said Letters Patent is hereby corrected as shown below:

Title page, between (63) Related U.S. Application Data and (51); insert
-- (30) Foreign Application Priority Data
Nov. 26, 1980   (DE)   Fed. Rep. of Germany       3044525 --.

Col. 2, lines 23 & 24; "substances" should read -- membranes --
Col. 2, line 41; "contents" should read -- content --
Col. 3, line 38; "22 200°" should read -- >200° --
Col. 4, line 26, last column; "5.66" should read -- 5.56 --
Col. 5, line 52; ".200γ/0.02 ml" should read -- 200γ/0.02 ml --
Col. 6, line 9; "table;" should read -- table: --
Col. 7, lines 10-14 (beginning with "It" and ending with "art."; delete the whole paragraph.
Col. 8, line 43; "threated" should read -- treated --
Col. 10, line 18; insert before "We claim:" this paragraph -- It is to be understood that the invention is not to be limited to the exact details of operation or exact compounds, compositions, methods, or procedures shown and described, as obvious modifications and equivalents will be apparent to one skilled in the art. --

UNITED STATES PATENT AND TRADEMARK OFFICE
CERTIFICATE OF CORRECTION

PATENT NO. : 4,602,037

DATED : July 22, 1986

INVENTOR(S) : Arthur Scherm and Klaus Hummel

PAGE 2 of 2

It is certified that error appears in the above-identified patent and that said Letters Patent is hereby corrected as shown below:

Col. 10, line 39; "claim 1" should read -- claim 20 --
Col. 10, line 41; "claim 1" should read -- claim 20 --
Col. 10, line 51; "claim 1" should read -- claim 20 --
Col. 10, line 53; "claim 1" should read -- claim 20 --
Col. 10, line 55; "claim 1" should read -- claim 20 --
Col. 11, line 8; "claim 1" should read -- claim 20 --

Col. 12, line 29; "mixture" should read -- xanthate --

Col. 13, line 3; insert a comma -- , -- after "vaccinia"
Col. 13, line 6; insert a comma -- , -- after "vaccinia"
Col. 13, line 19; delete "as"
Col. 13, line 20; delete the whole line
Col. 14, line 5; delete "as"
Col. 14, line 6; delete the whole line
Col. 14, line 15; "infuenza" should read -- influenza --

Signed and Sealed this

Ninth Day of December, 1986

*Attest:*

DONALD J. QUIGG

*Attesting Officer*  *Commissioner of Patents and Trademarks*